(12) United States Patent
Chevallier et al.

(10) Patent No.: US 8,771,235 B2
(45) Date of Patent: Jul. 8, 2014

(54) SYRINGE DEVICE WITH PROTECTIVE CAP

(75) Inventors: Stéphane Chevallier, Saint Soupplets (FR); Jean-Michel Chevallier, Enghien-les-Bains (FR)

(73) Assignee: Tech Group Europe Limited, Dublin (IE)

( * ) Notice: Subject to any disclaimer, the term of this patent is extended or adjusted under 35 U.S.C. 154(b) by 484 days.

(21) Appl. No.: 12/254,266

(22) Filed: Oct. 20, 2008

(65) Prior Publication Data

US 2009/0105661 A1   Apr. 23, 2009

(30) Foreign Application Priority Data

Oct. 23, 2007  (FR) ...................................... 07 58496

(51) Int. Cl.
*A61M 5/32* (2006.01)

(52) U.S. Cl.
USPC ........... 604/192; 604/197; 604/198; 604/110; 604/164.08; 604/263

(58) Field of Classification Search
USPC ......... 604/181, 187, 192–198, 110, 263, 171, 604/164.08, 164.12
See application file for complete search history.

(56) References Cited

U.S. PATENT DOCUMENTS

| 4,871,355 A * | 10/1989 | Kikkawa ........................ 604/198 |
| 7,097,636 B2 * | 8/2006 | Pessin ........................... 604/187 |
| 2005/0148933 A1 * | 7/2005 | Raven et al. ................... 604/111 |
| 2006/0184133 A1 * | 8/2006 | Pessin ........................... 604/198 |

FOREIGN PATENT DOCUMENTS

| EP | 1 532 997 A1 | 5/2005 |
| FR | 2 762 790 A | 11/1998 |
| FR | 2 807 665 A | 10/2001 |
| WO | WO 03/077977 A2 | 9/2003 |
| WO | WO 2006/027445 A1 | 3/2006 |

OTHER PUBLICATIONS

Office Action issued Oct. 24, 2013 in U.S. Appl. No. 11/861,567 by Pessin.
Int'l Preliminary Report on Patentability issued Dec. 12, 2013 in Int'l Application No. PCT/US2012/039385.

* cited by examiner

*Primary Examiner* — Edelmira Bosques
(74) *Attorney, Agent, or Firm* — Panitch Schwarze Belisario & Nadel LLP

(57) ABSTRACT

The invention comprises a syringe body (10) having a distal end (10B) fitted with an injection needle (14), at least one sheath (16, 18) inside which the body is positioned, and a protective cap (40) able to be retained relative to the syringe body (10) to cover the needle (14) and be separate from this body to release the needle. The device comprises a non-return unit (50) able to oppose a refitting of the cap (40) in its protection position once the needle has been released. This non-return unit, for example, comprises an elastic lip (50) joined to the sheath or the cap.

7 Claims, 3 Drawing Sheets

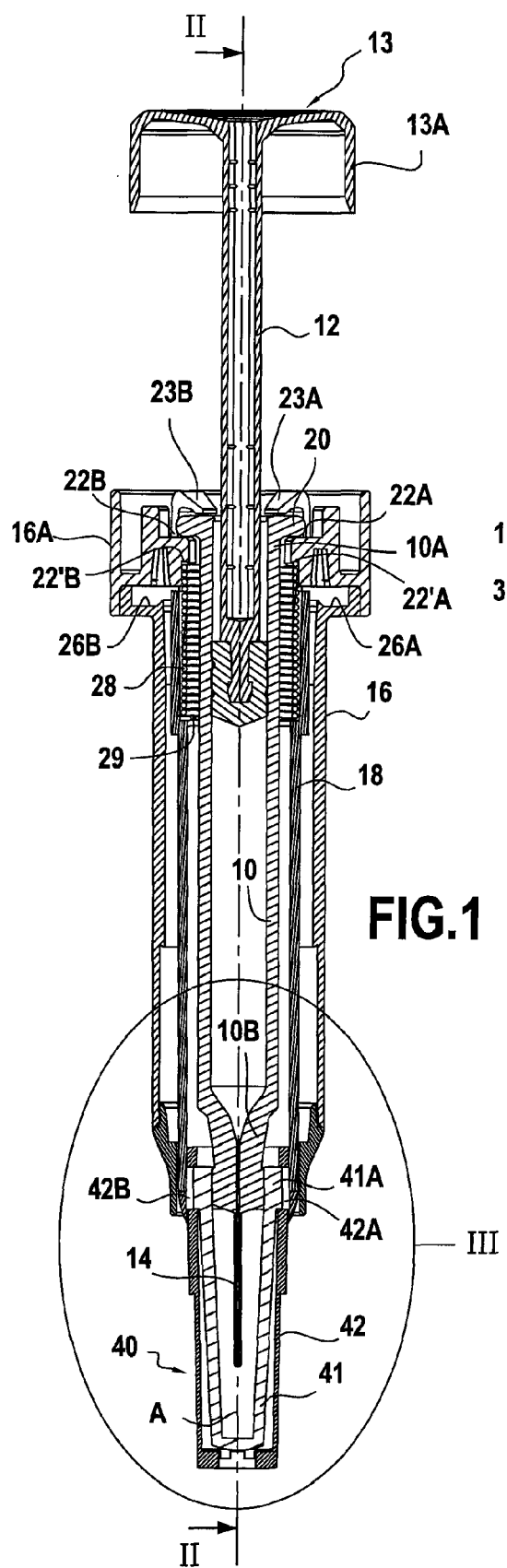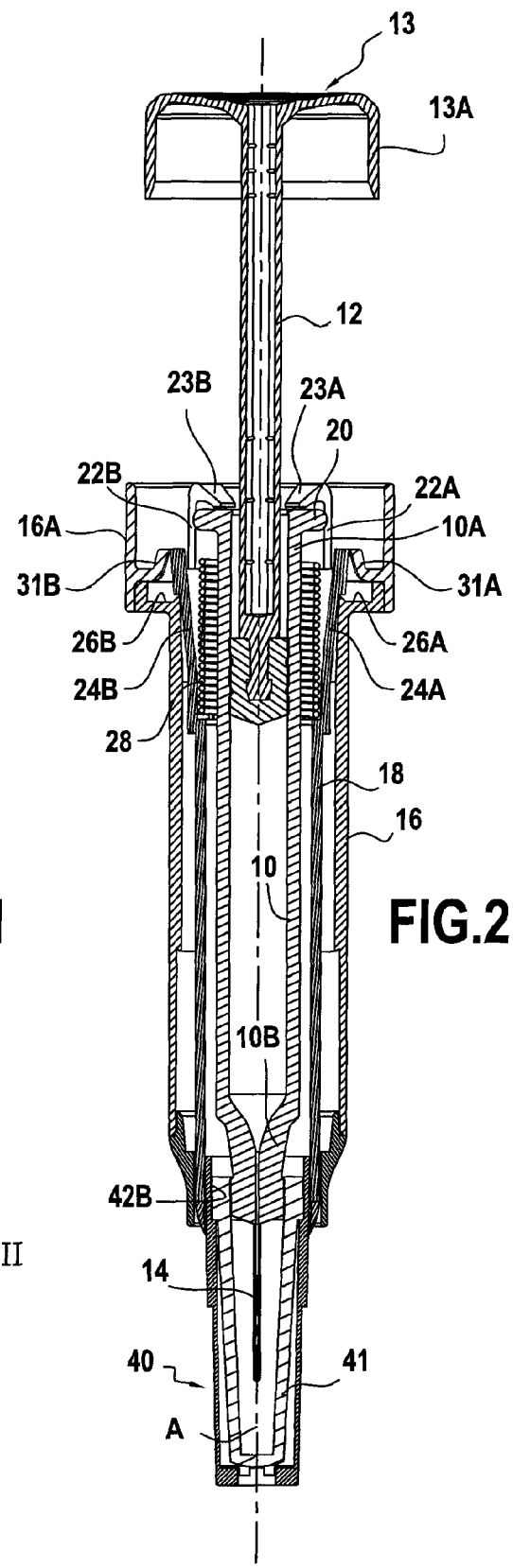

SYRINGE DEVICE WITH PROTECTIVE CAP

The present invention relates to a syringe device comprising a syringe body having a distal end fitted with an injection needle, at least one sheath inside which this body is positioned, and a protective cap, able to occupy a protection position in which the cap is retained relative to the syringe body so as to cover the needle and be separate from this body to release the needle, the device comprising a non-return unit, able to oppose a refitting of the cap in its protection position once the needle has been released.

Devices of this type are known. The sheath can be a simple support sheath, used to maintain the syringe body within it. It can also be a safety device, in which case it can comprise a protection sleeve which, at the end of injection, is placed around the needle by a relative sliding of this sleeve and the syringe body, so as to prevent the user being pricked with the needle. In this case, the abovementioned sheath can be this protection sleeve, or even a support sleeve used to maintain the syringe body, in which case the support sleeve and the protection sleeve are able to slide relative to each other.

The syringe body used in the inventive syringe device is in particular a pre-filled syringe body, for single use. In this case, it is important to check, before making the injection, that the syringe has not yet been used. It is in particular important to check that the needle could not have been soiled by an external contamination, whether inadvertently or following a malicious act. For this, it is necessary for a syringe device which could have been used or even whose needle could have been soiled not to be presented as a syringe device that has never before been used.

To ensure that the user of the device can easily check that the latter has not been used previously or that the needle is not soiled, WO 2006/027445 provides for equipping the protective sheath with tongues which, at rest, delimit an opening smaller than that of the cap, so as to prevent an easy refitting of the cap. The same applies for EP 1 532 997 and WO 03/077977.

This prior art device does not give entire satisfaction because, depending on the number of tongues, it is possible, manually, to force them all apart, even break one or more of them to refit the cap.

The aim of the invention is to improve this state of the art by choosing the structure of the non-return unit to make the refitting of the cap virtually impossible, or at least much more difficult.

This aim is achieved thanks to the fact that the non-return unit comprises an elastic lip which is joined to one of the elements formed by the sheath and the cap and which forms a closed ring, said lip being elastically constrained when the cap is in its protection position and adopting, in the free state, when the cap is separated from the body, a configuration able to oppose the refitting of the cap in the protection position.

This elastic lip can be easily added to the element that bears it by overmolding, gluing, or any other permanent fixing means. It is therefore very easy to make and fit, while forming a simple and effective means of opposing a refitting of the cap once the latter has been removed to release the needle.

Since the lip forms a closed ring, and is therefore continuous, it is necessary, to make its diameter compatible with the refitting of the cap, to modify this diameter uniformly. This is almost impossible by manual effort since the fingers cannot uniformly surround such a lip around its entire rim to uniformly modify its diameter.

To use the device or soil the needle, it is necessary to separate the cap from the syringe body and free the needle. Once this is done, the elastic lip of the invention effectively opposes a refitting of the cap. The user can therefore easily check before any first use whether the cap is correctly in place or not, the latter indicating a prior use or a soiling of the needle.

Advantageously, the cap cooperates by press-fitting with the distal end of the sheath and, in the free state, the elastic lip has diametral dimensions opposing this press-fitting.

As will be seen hereinafter, the lip can be joined to the cap, in which case its diametral dimensions in the free state can be too great to allow it to be press-fitted into the sleeve. It can, conversely, be joined to the sheath, in which case its diametral dimensions in the free state can be too small to allow the insertion of the cap by press-fitting into the distal end of the sheath.

Advantageously, the free end of the elastic lip is thinned.

This enhances the elastic return properties of the lip by ensuring that its thicker portion is joined to the element that supports it. The lip can have a cross section that is roughly in the form of a comma.

Advantageously, the sheath is a support sleeve relative to which the syringe body is retained.

As a variant, advantageously, the sheath is a protection sleeve, the syringe body and the protection sleeve being able to slide relative to each other, so as to occupy a waiting position, in which the free end of the needle extends beyond the sheath and a protection position in which the sheath is positioned around the free end of the needle.

It is advantageous for the device to comprise a support sleeve relative to which the syringe body is retained, and a protection sleeve, the syringe body and the protection sleeve being able to slide relative to each other, so as to occupy a waiting position in which the free end of the needle extends beyond the protection sleeve and a protection position in which the protection sleeve is positioned around the free end of the needle.

In this case, the sheath is advantageously formed by one of the elements comprising the support sleeve and the protection sleeve.

The invention will be well understood and its advantages become more apparent from reading the detailed description that follows, of embodiments represented by way of nonlimiting examples. The description refers to the appended drawings, in which:

FIG. 1 is a longitudinal cross-sectional view of a syringe device according to the invention, before its first use;

FIG. 2 is a longitudinal cross-sectional view, taken in the plane II-II indicated in FIG. 1;

Figure 5:
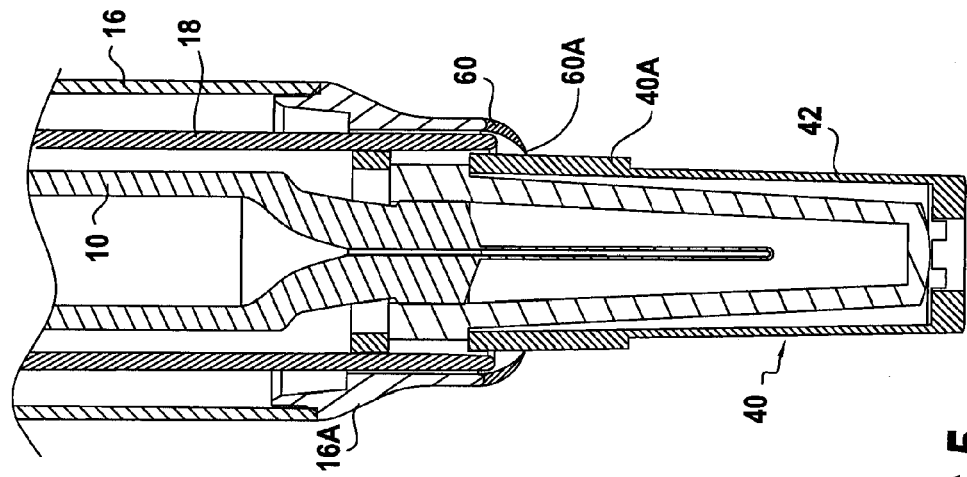
Figure 4:
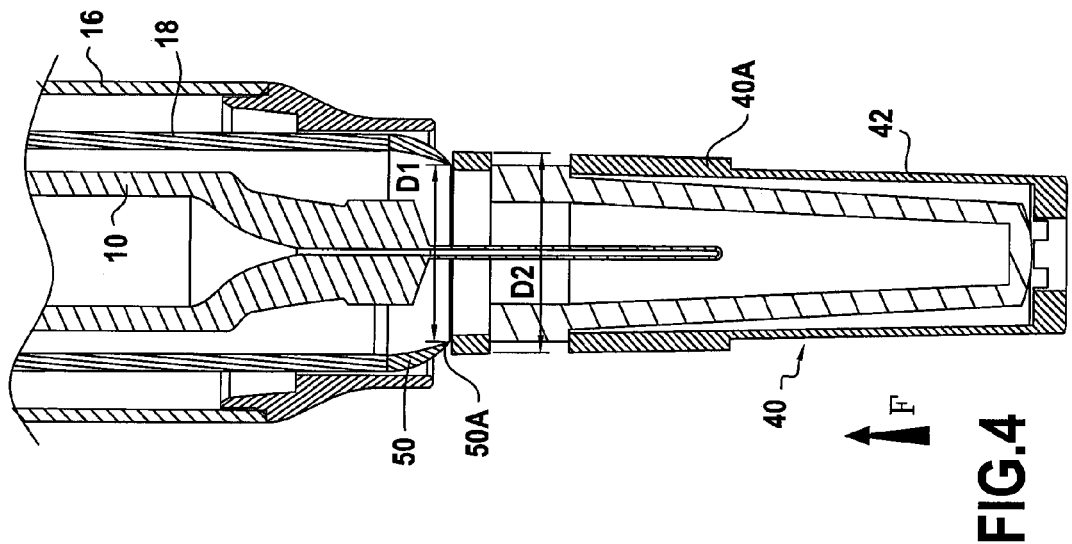
FIG. 4 shows the same zone as FIG. 3, whereas the cap has been removed and an attempt is being made to refit it.
Figure 3:
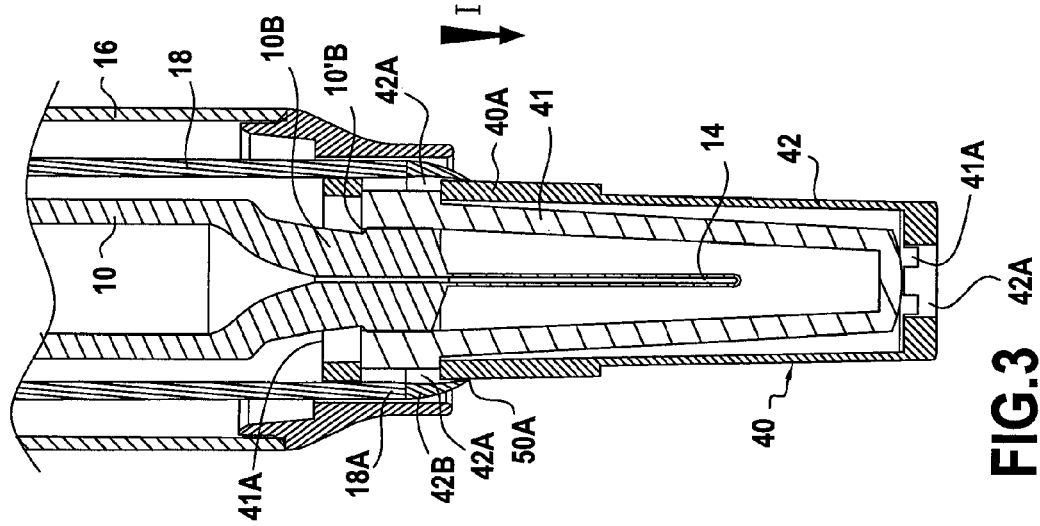
FIG. 3 is an enlargement of the zone III of FIG. 1.
Figure 8:
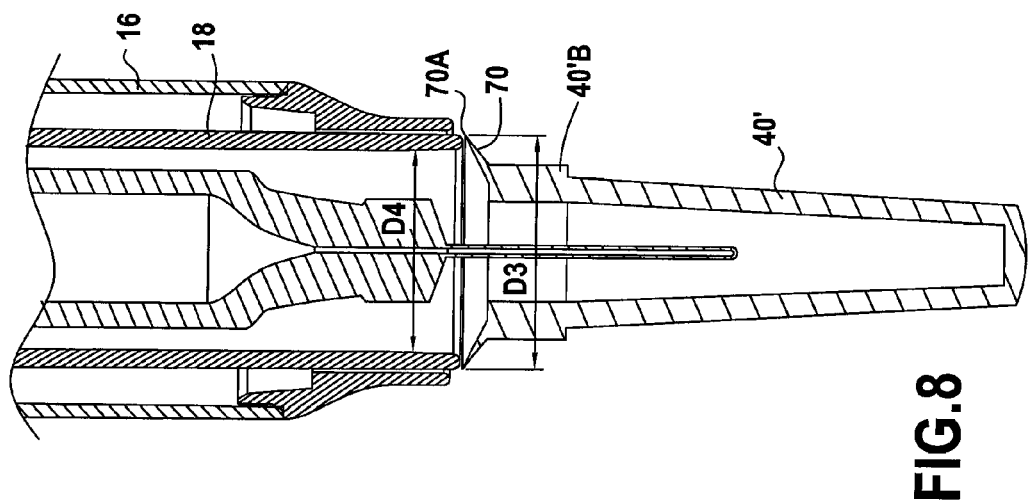
Figure 7:
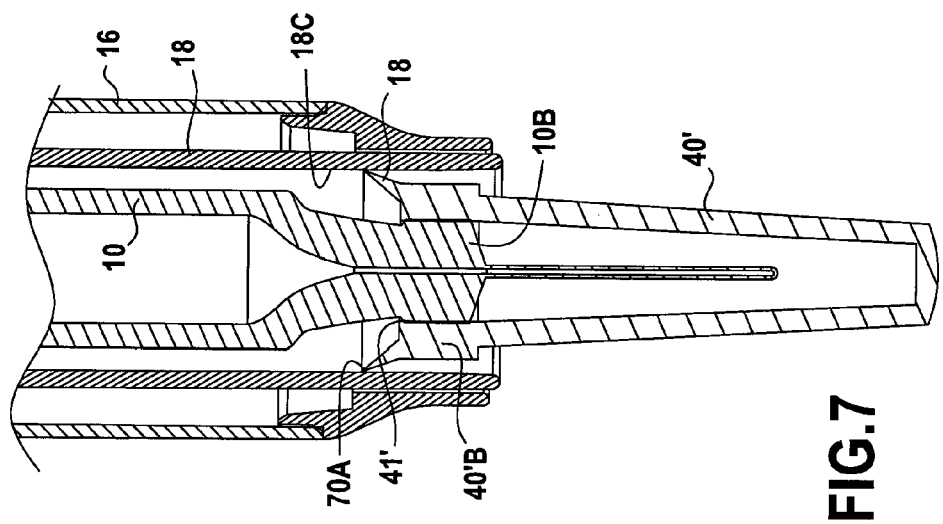
Figure 6:
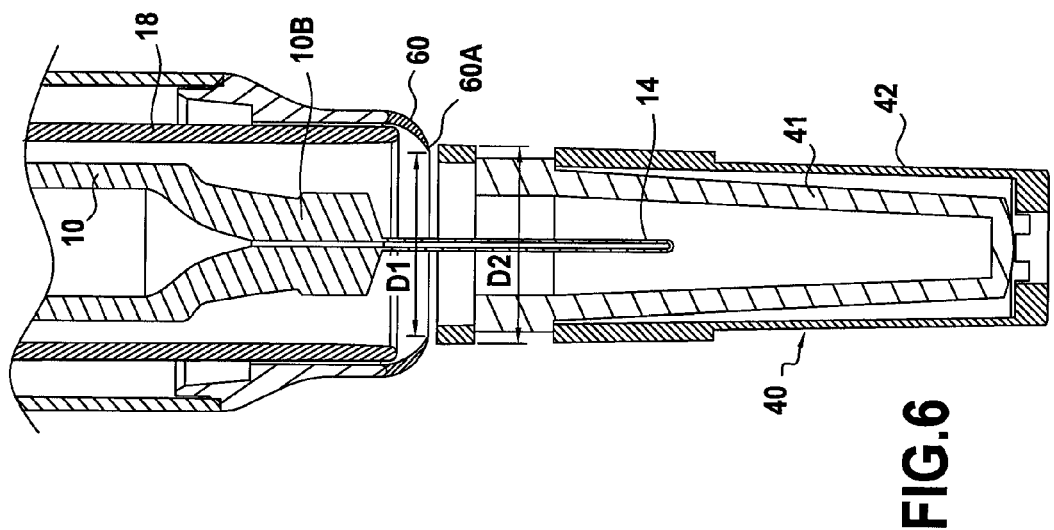

FIGS. 5 and 6 are views that are respectively similar to FIGS. 3 and 4 for another embodiment; and FIGS. 7 and 8 are views that are respectively similar to FIGS. 3 and 4, for yet another embodiment.

The device represented in FIGS. 1 and 2 comprises a syringe body 10 in which a piston 12 can slide by being inserted into the body from its proximal end 10A. At its distal end 10B, the body is fitted with an injection needle 14. The syringe body is, for example, made of plastic or glass.

Within the meaning of the present invention, the proximal end of an element is that which is closest to the fingers of a user making an injection with the device, whereas the distal end is the opposite end.

In the example represented, the syringe device is a safety device, of the type described in the patent application PCT WO 03/068298. In practice, it comprises an external support sleeve 16 relative to which the syringe body 10 is retained, and an internal protection sleeve 18 which, at the end of injection, can slide between the external support sleeve and the syringe body to be positioned around the needle 14 and so protect the user from being unfortunately pricked. The figures show the protection sleeve in the retracted position inside the support sleeve.

At its proximal end 10A, the syringe body has a radial collar 20 which is locked between, on the one hand, two shoulder portions 22A and 22B belonging to a proximal portion 16A of the support sleeve and, on the other hand, elastic retaining tabs 23A and 23B also belonging to this portion 16A.

Moreover, as can be seen in FIG. 2, the protection sleeve 18 has, at its proximal end, retaining tabs 24A and 24B which are attached to shoulder surfaces 26A and 26B of the proximal portion 16A of the support sleeve. A return spring 28 is positioned between an internal shoulder 29 of the protection sleeve 18 and the internal faces 22'A and 22'B of the shoulders 22A and 22B of the portion 16A of the sleeve 10. Moreover, in the example represented, actuating tabs 31A and 31B are joined to the portion 16A. It will be understood that, when the piston 12 arrives at the end of injection, the skirt 13A of its head 13 pushes back the actuating tabs 31A and 31B towards the axis A of the device, thus also pushing back the retaining tabs 24A and 24B towards this axis, so as to detach the protection sleeve 18 and allow the latter to be advanced to its protection position under the effect of the effort exerted by the spring.

The mechanism that has just been described to ensure the safety of the device by surrounding the needle at the end of an injection has been described purely as an example. As a general rule, it is possible to use, to provide the protection, any type of device comprising a support sleeve relative to which the syringe body will be retained and a protection sleeve, these sleeves being arranged so that, at the end of injection, the protection sleeve and the syringe body can slide relative to each other in order to ensure the protection of the needle. For example, it is possible for the whole comprising the syringe body and the support sleeve to go back in the direction from the distal end to the proximal end at the end of an injection to return the needle into the distal end of the protection sleeve. The support sleeve can be the only sheath and, by itself, provide the protection, for example by enabling a return of the syringe body relative to this sheath at the end of injection.

Generally, the device of the invention applies to any type of syringe device in which a syringe body is positioned inside a sheath, whether or not this sheath is used to provide protection. As will be seen hereinafter, the sheath in the sense of the invention can, for example, comprise the support sleeve or even the protection sleeve that has just been described, when the device comprises a protection arrangement.

When this is not the case, the sheath in the sense of the invention can comprise a simple support sleeve.

As can be seen in FIGS. 1 to 3, the device of the invention comprises a protective cap 40 which, in these figures, is represented in its protection position in which it is retained relative to the syringe body such that a distal end of the cap 40 is located at a shortest distance, as measured along a longitudinal axis of the needle, from a distal end of the needle 14 so as to cover the needle 14. In this case, this cap comprises an internal cap part 41 which is press-fitted around the distal end 10B of the syringe body and the only opening of which is that which delimits its press-fitting edge 41A located at its proximal end. Conventionally, this internal cap part 41 has a relative elasticity, enabling it to be naturally retained by catching behind a slight bulge 10'B of the distal end 10B of the syringe body 10. The cap even has an external cap portion 42 which is joined to the internal portion 41. More specifically, the external portion 42 has lateral windows 42A, 42B which are diametrically opposed and in which is blocked a section 41A of the portion 41, this section 41A having for this purpose an enlarged diameter. Between the windows 42A and 42B, the wall 42C of the external portion 42 is thinned.

Of course, other forms of cap can be envisaged. The cap is an element that covers the needle and therefore, overall, has a cover form suited to this function. It can be made of a single part or several parts. It also has a configuration enabling it to be removably joined with the distal end of the syringe body.

The device of the invention comprises a non-return unit which opposes a refitting of the cap 40 in its protection position once the needle has been released, that is, once this cap has been separated from the syringe body to enable access to the needle, in particular for an injection.

This non-return unit comprises an elastic lip. More specifically, in the embodiment represented in FIGS. 1 to 4, an elastic lip 50 is joined to an end portion 18A of the protection sleeve 18. It can be seen in FIGS. 1 to 3 that, when the cap 40 is in its protection position, the free end 50A of the lip is bearing against the external periphery 40A of the cap.

On the other hand, in FIG. 4, the cap 40 has been released, and the free end 50A of the lip 50 has naturally, under the effect of its elasticity, returned to a free-state configuration in which it delimits diametral dimensions D1 smaller than the diametral dimensions D2 of the external periphery of the cap in its zone of engagement with the sheath (in this first embodiment, the sheath is the protection sleeve 18). Thus, when an attempt is made to refit the cap by press-fitting into the distal end portion of the protection sleeve 18 by pushing in the direction F indicated in FIG. 4, the lip 50 opposes this refitting.

It is important to note that the syringe body is initially pre-fitted with the cap 40 and that the syringe body as well as the cap have maximum diametral dimensions that enable their insertion into the whole comprising the support sleeve and the protection sleeve through the proximal end of these sleeves, in the direction of the arrow I indicated in FIG. 3. Thus, the lip 50 does not oppose this fitting, but the insertion of the syringe body and the cap into the sleeves elastically separates this lip to constrain it elastically expansion-wise so that its free end 50A is flattened against the external wall of the cap.

In FIGS. 5 and 6, the elastic lip 60 is joined to the distal end portion 16A of the support sleeve 16. In FIG. 5, it can be seen that the free end 60A of the lip is bearing against the external periphery 40A of the cap 40 when the cap is in its protection position, before a first use of the device. This lip is then more curved than in the example of FIGS. 1 to 4, to make up the play corresponding to the thickness of the internal protection sleeve 18.

In FIG. 6, the cap has been removed for the needle 14 to be released, and it can be seen that the free end 60A of the lip 60 delimits diametral dimensions D1 smaller than the diametral dimensions D2 of the external periphery of the cap in its zone of engagement with the sleeve 16, so that this lip opposes the refitting of the cap.

In FIGS. 7 and 8, the elastic lip 70 is joined to a proximal end portion 40'B of the cap 40'. In this case, this cap has the form of a simple cover, and is produced in a single part. This shape is therefore globally similar to that of the internal portion 41 of the cap 40 described in the preceding figures, except that its proximal end bears the abovementioned lip. It can be seen, in FIG. 7, that the cap is retained relative to the syringe body by being press-fitted by force around the distal end 10B of this body, by being retained by a slight catching effect on its internal bead 41' in an annular groove 10'B of said distal end 10B. In this position, the lip 70 is constrained in the direction of a reduction of its diametral dimensions. In practice, its free end 70A bears against the internal periphery 18C of the protection sleeve 18.

As can be seen in FIG. 8, once the cap 40' has been separated from the rest of the device, the lip 70 returns elastically to its free-state configuration, in which its free end 70A delimits diametral dimensions D3 greater than the diametral dimensions D4 of the internal periphery 18C of the protection sleeve 18 in its zone of engagement with this lip. Consequently, it is no longer possible to press-fit the proximal end of the cap 40' inside this sleeve. If an attempt is made to force the fitting of the cap, the lip 70 tends to turn back on itself and then forms, on the edge of the cap, an overthickness that opposes the press-fitting of the cap onto the end of the device.

In the example that has just been described, the free end 70A of the lip 70 cooperates with the internal periphery of the protection sleeve 18 when the cap is in its protection position. Obviously, it would be possible to choose a different configuration, by ensuring that this free end cooperates rather with the internal periphery of the support sleeve 16. For this, it would be sufficient, in its retracted position inside the support sleeve, for the protection sleeve to be less advanced toward the distal end.

Generally, the sheath that bears the elastic lip (embodiments of FIGS. 1 to 6) or that cooperates with the elastic lip supported by the cap (embodiments of FIGS. 7 and 8) can be the support sleeve or even the protection sleeve.

The elastic lip is advantageously made of plastic material conferring on it the required elasticity. It can be, for example, a material of elastomer or rubber type.

In the case of FIGS. 7 and 8, the lip 70 can be made in a single piece with the rest of the cap 40', by monoblock molding (in which case, all of the cap is produced in the same material), or even added to the cap, for example by overmolding or gluing.

The invention claimed is:

1. A syringe device comprising:
    a syringe body having a distal end fitted with an injection needle;
    at least one sheath inside which the syringe body is positioned;
    a protective cap having:
        (i) a protection position, wherein the cap is retained relative to the syringe body such that a distal end of the cap is located at a shortest distance, as measured along a longitudinal axis of the needle, from a distal end of the needle so as to cover the needle, movement of the distal end of the cap with respect to the distal end of the needle from the protection position being limited to a distal direction along the longitudinal axis, and
        (ii) a free state, wherein the cap is separated from the syringe body to release the needle; and
    an elastic lip joined to the sheath and which forms a closed ring having a free end, the lip being elastically constrained wherein the free end defines a first diameter when the cap is in the protection position and defines a second diameter in the free state, the second diameter being smaller than the first diameter to oppose refitting of the cap in the protection position once the needle has been released, wherein in both the protection position and the free state, the free end of the elastic lip is located distally of the joint of the elastic lip with the sheath.

2. The device as claimed in claim 1, wherein, in the protection position, the cap cooperates by press-fitting with the distal end of the sheath.

3. The device as claimed in claim 2, wherein the elastic lip is joined to a distal end portion of the sheath and the free end, when the cap is in its protection position, bears against the external periphery of the cap, whereas, in the free state of the elastic lip, said free end delimits diametral dimensions less than diametral dimensions of the external periphery of the cap.

4. The device as claimed in claim 3, wherein the free end of the elastic lip is thinned.

5. The device as claimed in claim 1, wherein the sheath is a protection sleeve, the syringe body and the protection sleeve being able to slide relative to each other, so as to occupy a waiting position, in which a free end of the needle extends beyond the sheath and a protection position in which the sheath is positioned around the free end of the needle.

6. The device as claimed in claim 1, comprising a support sleeve relative to which the syringe body is retained, and a protection sleeve, the syringe body and the protection sleeve being able to slide relative to each other, so as to occupy a waiting position in which the free end of the needle extends beyond the protection sleeve and a protection position in which said sleeve is positioned around the free end of the needle.

7. The device as claimed in claim 6, wherein the sheath is formed by one of the elements comprising the support sleeve and the protection sleeve.

* * * * *